(12) United States Patent
Burkett et al.

(10) Patent No.: US 6,649,144 B1
(45) Date of Patent: Nov. 18, 2003

(54) METHOD FOR DETECTING AND KILLING EPITHELIAL CANCER CELLS

(75) Inventors: Douglas D. Burkett, Phoenix, AZ (US); Ralph E. Green, Scottsdale, AZ (US); Samuel D. Bernal, Woodland Hills, CA (US)

(73) Assignee: Zila, Inc., Phoenix, AZ (US)

( * ) Notice: Subject to any disclaimer, the term of this patent is extended or adjusted under 35 U.S.C. 154(b) by 0 days.

(21) Appl. No.: 09/673,991
(22) PCT Filed: Feb. 28, 2000
(86) PCT No.: PCT/US00/05387
§ 371 (c)(1), (2), (4) Date: Apr. 5, 2001
(87) PCT Pub. No.: WO01/64110
PCT Pub. Date: Sep. 7, 2001
(51) Int. Cl.[7] ............................................... A61K 51/00
(52) U.S. Cl. ........................... 424/9.1; 424/9.6; 424/9.8
(58) Field of Search ................... 424/9.1, 9.6, 9.7, 424/9.8; 514/222.2, 226.2, 226.8, 227.5, 258

(56) References Cited

U.S. PATENT DOCUMENTS 4,816,395 A * 3/1989 Hancock et al. ............... 435/29
5,372,801 A * 12/1994 Malmros et al. ............. 424/7.1

OTHER PUBLICATIONS

Bernal, S. et al., Anticarcinoma activity in vivo of rhodamine 123, a mitochondrial–specific dye, Science, vol. 222, pp. 169–172, Oct. 1983.*

* cited by examiner

Primary Examiner—Michael G. Hartley
(74) Attorney, Agent, or Firm—Drummond & Duckworth

(57) ABSTRACT

A diagnostic method for detecting cancerous epithelial cells by selectively marking the mitochondria of the cancer cells, by delivering to the epithelium a cationic supravital mitochondrial marking agent. Selective killing of cancerous epithelial cells in the presence of normal cells is effected by delivering a cationic supravital mitochondrial marking agent to epithelial cancer cells. The killing agent can also comprise the reaction product of the marking agent and a cancer chemotherapeutic drug.

1 Claim, No Drawings

METHOD FOR DETECTING AND KILLING EPITHELIAL CANCER CELLS

This application is a 371 of PCT/US00/05387, filed Feb. 28, 2000.

FIELD OF THE INVENTION

This invention relates to methods for detecting epithelial cancer.

In another respect the invention pertains to methods for selectively killing epithelial cancer cells.

In a further aspect, the invention concerns methods for detecting epithelial cancer cells in the presence of normal cells and/or for selectively killing such cells, in which the mitochondria of cancer cells retains a mitochondrial marking agent for a time sufficient to permit identification and/or killing such cells.

DEFINITIONS

As used herein, the following terms have the indicated meanings:

"Cancer" or "cancerous" cells are used in the broad sense, to include invasive cancer cells, cancer-in-situ cells and severely dysplastic cells.

"Mitochondrial marking agent" means a compound that is selectively taken up by the mitochondria of living cancer cells and is selectively retained in cancer cells for a time sufficient to permit identification and/or killing or incapacitation thereof.

"Killing" of cells means either causing cell death or cell changes that render a cell incapable of reproduction and metastasizing.

"Adduct" means the reaction product of a mitochondrial marking agent and a cancer chemotherapeutic agent.

BACKGROUND OF THE INVENTION

In-vivo diagnostic procedures for detecting malignant and premalignant epithelial lesions or carcinomas, employing dye compositions that selectively "color" tissues that are abnormal due to dysplasia, hyperplasia, tumorigenesis and other active surface lesions, are known in the art. These diagnostic methods employ a dye that imparts color to a cancerous substrate, which is then detectable under light at visible wavelengths or a fluorescent dye that imparts color to the substrate, which is then detectable when illuminated by light at wavelengths outside the visible spectrum.

For example, procedures employing fluorescein and fluorescein derivatives are disclosed in Chenz, Chinese Journal of Stomatology (27:44–47 (1992)) and Filurin (Stomatologiia (Russian) 72:44–47 (1993)). These procedures involve application of the dye, followed by examination under ultraviolet light to detect the cancerous/precancerous tissue, which is selectively fluorescent. Another prior art procedure involves rinsing the epithelium with toluidine blue, followed by normal visual examination to detect any selectively stained tissue. Such procedures are disclosed, for example in the patents to Tucci et al. (U.S. Pat. No. 5,372,801) and Mashberg (U.S. Pat. No. 4,321,251). Use of certain other thiazine dyes and oxazine dyes in an analogous manner is disclosed in U.S. Pat. No. 5,882,627 to Pomerantz.

Heretofore, it was theorized that such dyes selectively "marked" cancerous tissue because it was retained in the relatively larger interstitial spaces between the cells of cancerous tissue and would not efficiently penetrate the normally tight intracellular junctions of normal tissue or be selectively retained in such relatively smaller spaces.

Contrary to the belief that toluidine blue selectively marks cancerous epithelial tissue because it is selectively retained in the relatively larger interstitial spaces between cancer cells, the mechanism of such selective staining of epithelial tissue by cationic dyes, e.g., dyes such as rhodamine, fluoresceins, oxazine and thiazine dyes (including toluidine blue) and other cationic supravital marking agents is the selective uptake and selective retention of the agent in the mitochondria of cancer cells. In turn, this selective staining of and retention in the mitochondria is apparently due to the higher electrical potential (negative charge on the inside of the membrane) of cancerous mitochondrial cells as compared to normal cells. See, e.g., Chen et al., Cancer Cells 1/The Transformed Phenotype, 75–85 (Cold Spring Harbor Laboratory, 1984); Lampidis, et al., Cancer Research 43, 716–720 (1983).

In fact, the selective marking and retention of the mitochondria of cancer cells by supravital cationic dyes and other supravital cationic marking agents are related to one of the very characteristics of cancer cells that appears to be responsible for their rapid cloning growth and metastasizing ability, namely, that the higher electrical potential of the mitochondria of cancer cells is the source of cellular energy and is the driving force for ATP (adenosine triphosphate) product of the cells.

SUMMARY OF THE INVENTION

I have now discovered a method for in-vivo detection of cancerous epithelial cells by selective marking of the mitochondria thereof. My method comprises the steps of delivering to tissue in the locus of a suspect cancerous site on the epithelium (which contains both normal and cancerous cells), with a cationic supravital mitochondrial marking agent other than rhodamine, causing said agent to be taken up and selectively retained in the mitochondria of cancer cells. The cancerous cells are then detectable by any suitable method, for example, instrumental or visual examination under visible light or under light of selected invisible wavelengths.

In a further embodiment, after the marking agent is taken up by the mitochondria, a rinse reagent is applied to the locus of the suspect cancerous site, thus enhancing the rate of release of the agent from the mitochondria of the normal cells and further increasing the selectivity of the diagnostic method.

According to another embodiment of the invention, I provide a method for selectively killing cancerous epithelial cells comprising the step of contacting cancerous cells in the locus of a suspect cancerous site with a cationic supravital mitochondrial marking agent, to cause cell death or to render the cancer cells substantially incapable of multiplication. The marking agent can be delivered to the cancer cells in a single discrete dose, or continuously, or in repeated discrete doses, with or without employing a rinse reagent after each dose.

In a further embodiment of the invention, I provide a method of improving the selectivity of cancer chemotherapeutic agents comprising the steps of forming an reaction product of a cationic supravital agent and a chemotherapeutic agent and delivering the reaction product to cancerous epithelial cells.

These, other and further embodiments of the invention will be apparent to those skilled in the art and a better understanding of the invention will be obtained from the following examples which are provided to illustrate the invention and not as indications of the scope thereof, which is defined only by the appended claims.

In the following working examples, cationic supravital mitochondrial marking agents, including

- dyes, including toluidine blue O, alcian blue, malachite green, phenosafranin, acriflavine, pyronine Y, toluylene blue and brilliant green; and
- "non-dye" compounds, including peonidin, oxythiamine, tiemonium iodide, elliptinium acetate and furazolium chloride.

In order to be selectively absorbed and retained in cancer cell mitochondria, the marking agent or reaction product of marking agent+chemotherapeutic agent, must have a molecular weight of below about 5,000.

EXAMPLE 1

Uptake and Retention of Mitochondrial Marking Agents in Living Carcinoma Cells

Different concentrations of the various cationic marking agents, at 100, 50, 10 and 1 μg/ml are prepared in RPMI medium complete with 20% fetal calf serum, 1 mM glutamine, hydrocortisone, insulin, transferrin, estradiol, selenium and growth hormone.

The carcinoma cells are incubated at 37° C. in tissue culture incubators with 5% $CO_2$ and 95% relative humidity, for 5 minutes with each agent and concentration there and then rinsed twice using 2 minute incubations with 1% acetic acid. After incubation and rinsing, the cells are harvested, at 30 min., 1 hour, 2 hours, 4 hours and 8 hours. The cells are then extracted with 2-butanol and analyzed by spectrophotometry for quantitation of the marking agent.

The results show that there is a concentration dependence in the rate of accumulation of marking agent in the mitochondria of both carcinoma and normal cells and in the selectivity of release of the marking agent from cancer cells, but this concentration dependence starts to become less pronounced. The saturation concentration for toluidine blue O occurs at concentrations of 10 μg/ml and above. The saturation concentrations for the other marking agents are similarly determined. The remaining experiments are conducted with a concentration of 10 μg/ml for toluidine blue O and at the saturation concentrations for the other marking agents so-determined, unless stated otherwise.

EXAMPLE 2

Mitochondrial Localization of the Agents in Living Cells

After incubation and rinsing of various cell lines, using the different cationic marking agents, the mitochondrial localization of the agents is analyzed using confocal high resolution microscopy and phase contrast microscopy.

Living cells, are cultivated in complete growth medium with 20% fetal calf serum and growth factors, and maintained at 37° C. These cells accumulate and retain the marking agents in the mitochondria. When these cells are then maintained in a agent-free medium, carcinoma cells retain the agent for longer than about 1 hour, but normal epithelial cells release the agent within about 15 minutes.

In contrast to living cells, dead cells or cells treated with agents that dissipate the mitochondrial membrane potential lose mitochondrial staining and accumulate the agents in the nucleus.

EXAMPLE 3

Release of the Agents from Mitochondria With Dissipation of the Mitochondrial Membrane Potential Known agents that alter the mitochondrial electrical potential are used to pretreat epithelial cancer cells, followed by treatment with the cationic supravital mitochondrial marking agents. These pretreatment agents include azide and cyanide preparations and dinitrophenol.

Epithelial cancer cells are also pre-stained with the various dyes and then are post-treated with these known agents. The release of the dyes from the cells or the transfer of the dyes to other subcellular compartments, including the nucleus is analyzed.

The cells pretreated with these agents did not accumulate dyes in the mitochondria and the mitochondria of the pre-stained cells released the dye upon post-treatment with these agents.

EXAMPLE 4

Tissue Explants of Squamous Carcinomas

Fresh explants of resected epithelial carcinomas are analyzed for marking agent uptake and retention. After resection, the carcinomas are microdissected from surrounding tissue, cut into 3 mm sections and maintained as explant tissue cultures at 37° C. These explants are then incubated with the various agents and then extracted for quantitation of the agent.

Oral carcinoma (SqCHN) have rapid uptake and prolonged retention of these agents. The agents start to be released from the cells after about one hour of cultivation in agent-free medium. However, the agents are released faster when the cells are incubated in medium that does not contain growth factors, fetal calf serum and other medium additives. The agents are also released faster when the cells are grown in adverse conditions such as lower temperatures.

EXAMPLE 5

Tissue Explants of Normal Epithelial Cells

Cells obtained surgically from normal areas of the oral epithelium are cultivated as normal epithelial cultures. These cultures are then incubated with the marking agents for analysis of the agent uptake and retention.

Unlike the carcinoma cells, normal epithelial cells quickly release the agents from their mitochondria and from the cell much more quickly. By 10–15 minutes, most of the agent is released from the mitochondria.

EXAMPLE 6

Marking Agent-Chemotherapeutic Agent Adducts

In place of the agents of Examples 1–5, the following adducts of cationic mitochondrial marking agents and various known chemotherapeutic agents are employed, with substantially similar results, except that the cancer cell kill rate and selectivity of the chemotherapeutic agent substantially improved.

| Marking Agent | Chemotherapeutic Agent |
|---|---|
| toluidine blue 0 | methotrexate |
| rhodamine 123 | nitrogen mustard |

We claim:

1. A diagnostic method for in vivo detection of cancerous epithelial cells by selective marking of the mitochondria thereof, comprising the steps of: topically delivering to the epithelium a cationic supravital mitochondrial marking agent, said agent be a member of the group consisting of cationic supravital mitochondrial marking agents other than toluidine blue O; and detecting the retention of said agent by the mitochondria of cancerous and precancerous cells on said epithelium.

* * * * *